United States Patent [19]

Enomoto et al.

[11] 4,357,349

[45] Nov. 2, 1982

[54] HEPATIC CANCER PREVENTING AND TREATING MEDICINE FOR LOWER ANIMALS

[75] Inventors: Makoto Enomoto, Tokyo; Nobumichi Doke, Ibaraki, both of Japan

[73] Assignees: Nitto Chemical Industry Co.; Chemisciences Inc., both of Tokyo, Japan

[21] Appl. No.: 178,422

[22] Filed: Aug. 15, 1980

[30] Foreign Application Priority Data

Aug. 17, 1979 [JP] Japan .................................. 54/104091

[51] Int. Cl.$^3$ ...................... A61K 31/26; A61K 31/70
[52] U.S. Cl. .................................... 424/302; 424/180
[58] Field of Search ................................ 424/302, 180

[56] References Cited

PUBLICATIONS

Tasayama et al., IARC Scientific Publication, No. 16, pp. 271–286, (1977).
Wattenber, J. of the National Cancer Institute 60 (1), pp. 11–18, (1978).
Aoki et al., J. of the National Cancer Institute 59 (2), pp. 1747–1749, (1977).
Chemical Abstracts 84:150881m (1976).
Chemical Abstracts 88:51125u (1978).

*Primary Examiner*—Jerome D. Goldberg
*Attorney, Agent, or Firm*—Sughrue, Mion, Zinn, Macpeak & Seas

[57] ABSTRACT

A cancer preventing and treating medicine containing 2,3,4,5,6-penta-o-acetyl-D-gluconyl isothiocyanate as a major component.

3 Claims, No Drawings

HEPATIC CANCER PREVENTING AND TREATING MEDICINE FOR LOWER ANIMALS

BACKGROUND OF THE INVENTION

1. Field of the Invention

This invention relates to a medicine for preventing and treating hepatic cancer in lower animals, and more particularly to a medicine containing 2,3,4,5,6-penta-o-acetyl-D-gluconyl isothiocyanate as a major component.

2. Description of the Prior Art

A number of chemical and biochemical medicines for treatment of cancer have hitherto been reported. Many conventional medicines, however, are of limited value, in that the effectiveness in treating the cancer is poor, the toxicity is high, and/or it is necessary to administer large doses, thus, various problems have arisen in making practical use of such medicines.

It has therefore been the subject of a long and continuing search by those engaged in this field to develop cancer preventing and treating medicines which are free from the above-described problems of the prior art medicines, that is, medicines which exhibit lower toxicity and high effectiveness even when used in small dosages.

SUMMARY OF THE INVENTION

It has now been found according to this invention that 2,3,4,5,6-penta-o-acetyl-D-gluconyl isothiocyanate (hereinafter referred to as "GITC") significantly inhibits the growth of hepatic cancer in lower animals.

This invention, therefore, provides a medicine for preventing and treating hepatic cancer in lower animals which contains 2,3,4,5,6-penta-o-acetyl-D-gluconyl isothiocyanate as a major component.

DETAILED DESCRIPTION OF THE INVENTION 2,3,4,5,6-penta-o-acetyl-D-gluconyl isothiocyanate used in this invention can be produced, for example, by a method which comprises dissolving 2,3,4,5,6-penta-o-acetyl-D-gluconyl chloride in anhydrous xylene, adding silver thiocyanate thereto, and heating the resulting mixture with stirring, as described, for example, in Japanese Patent Application (OPI) No. 105123/77 (the term "OPI" as used herein refers to a "published unexamined Japanese patent application"). Produced thusly, the compound is obtained in the needle crystal form, has a melting point of 96° to 98° C., and has the following structural formula:

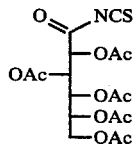

Although thus having been described, GITC has never before been proposed to use the substance for the prevention and treatment of hepatic cancer in lower animals.

GITC may be administered orally or non-orally and it can be used alone or in combination with other materials, such as extenders. It is preferred that it be used in the form of a capsule, a tablet, a powder, a granule, a vial, an ampoule, or the like. The dose may vary depending upon the conditions to be treated, compound used, response to the medication, etc., but the daily dose (average body weight: about 60 kg) usually ranges from about 0.5 g to 1 g in single or multiple dose.

The GITC compound of this invention is uniquely useful for the prevention and treatment of hepatic cancer in lower animals, as will hereinafter be explained in detail by reference to experiments.

The following Example 1 is provided to illustrate in greater detail that the GITC compound of this invention is useful for the treatment of hepatic cancer in lower animals.

EXAMPLE 1

In this experiment, cancer was produced in Himedaka (small aquarium fish: Oryzias latipes) by use of a diethyl nitrosamine (hereinafter referred to as "DENA") solution as reported by Ishikawa et al., and the treatment effect was tested.

It is disclosed in *Journal of the National Cancer Institute*, 55, 909–916 (1975), 59, 1747–1749 (1977) nad 60(1), 11–18 (1978) that when Himedaka is raised in a solution having a concentration of DENA of 15 to 135 ppm, it suffers from a liver tumor and that Himedaka is highly sensitive to carcinogenic substances. Further, in IARC SCIENTIFIC PUBLICATION, No. 16, pp. 271 to 286 (1977), it is disclosed that the experiment using piscine liver tumors can contribute to a study of the treatment of cancer.

According to studies conducted in this invention, when Himedaka is raised in a DENA aqueous solution having a concentration of 100 ppm for 4 weeks, a liver tumor is produced therein; many hypertrophic nodules of liver cell are first formed, and with the lapse of time of about 10 to 24 weeks, some of them develops into an adenoma or carcinoma.

Based upon the above findings, Himedaka was used for examining the carcinostatic or anti-cancer effect of GITC and the experiments were carried out under the conditions as illustrated in Table 1.

Further, in order to compare the GITC compound of this invention with the 5-fluorouracil (hereinafter referred to as "5-FU") as a conventional carcinostatic substance, the experiments using 5-FU were carried out as Groups V and VI.

TABLE 1

| Group | Zone | Application |
|---|---|---|
| I | Standard Zone | Raised in normal water (drinking water) with a normal feed [CE-2 produced by Japan CLEA (Central Laboratory of Experimental Animals)] |
| II | DENA Zone | Raised in a DENA aqueous solution (100 ppm) for 4 weeks and transferred to normal water. A normal feed is used. |
| III | GITC Zone | Raised in normal water with a feed containing 500 ppm of GITC. |
| IV | GITC Treating Zone | Raised in a DENA aqueous solution (100 ppm) for 4 weeks during which period a normal feed is given for the first two weeks, and a feed containing 500 ppm of GITC, for the remaining two weeks. |
| V | 5-FU Zone | Raised in normal water with a feed containing 100 ppm of 5-FU |
| VI | 5-FU Treating Zone | Raised in a DENA solution (100 ppm) for 4 weeks during which period a normal feed is given for the first two weeks, and a feed containing 100 ppm of 5-FU, for the remaining |

TABLE 1-continued

| Group | Zone | Application |
|-------|------|-------------|
|       |      | two weeks.  |

The Himedaka used was one-year-old, each group comprises fifty Himedaka, and the average length and weight thereof were respectively 28 mm and 250 mg. The amount of the feed administered is about 800 mg/day per one group being comprised of the fifty Himedaka.

After 4 and 10 weeks from the start of the experiment under the above-described conditions, part of the samples were removed and analyzed, and after 24 weeks the remaining samples were analyzed. The samples were killed and then fixed with a Bouins solution (a mixture of 15 ml of saturated aqueous solution of picric acid, 1 ml of glacial acetic acid and 5 ml of formalin), embedded in paraffin, sectioned at 5μin thickness, stained with hematoxylin and eosine, and morphological changes of the liver were examined with a microscope. The results are shown in Table 2.

TABLE 2

| | Observation (incidence of preneoplastic and neoplastic lesions) | |
|---|---|---|
| | 10 Weeks | 24 Weeks |
| Group I (Standard Zone) | Normal fish 100% | Normal fish 100% |
| Group II (DENA Zone) | Normal fish 0% | Normal fish 0% |
| | Liver Cell Nodule 62.5% | Liver Cell Nodule 53.8% |
| | Adenoma 25.0% | Adenoma 15.4% |
| | Carcinoma 12.5% | Carcinoma 30.8% |
| | (Tumor Ratio 37.5%) | (Tumor Ratio 46.2%) |
| Group III (GITC Zone) | Normal fish 100% | Normal fish 100% |
| Group IV (GITC Treating Zone) | Normal fish 70.0% | Normal fish 28.6% |
| | Liver Cell Nodule 20.8% | Liver Cell Nodule 52.4% |
| | Adenoma 4.6% | Adenoma 19.0% |
| | Carcinoma 4.6% | Carcinoma 0% |
| | (Tumor Ratio 9.2%) | (Tumor Ratio 19.0%) |
| Group V (5-FU Zone) | Normal fish 85.6% | Normal fish 86.4% |
| | Liver Cell Nodule 14.4% | Liver Cell Nodule 13.6% |
| Group VI (5-FU Treating Zone) | Normal fish 12.5% | Normal fish 15.1% |
| | Liver Cell Nodule 50% | Liver Cell Nodule 33.3% |
| | Adenoma 37.5% | Adenoma 18.3% |
| | Carcinoma 0% | Carcinoma 33.3% |
| | (Tumor Ratio 37.5%) | (Tumor Ratio 51.6%) |

As can be seen from Table 2, in Groups I and III wherein no DENA solution was used, no liver cell nodule and, of course, no tumors were observed after 10 and 24 weeks. On the other hand, for those of Group II which were raised in the DENA solution for 4 weeks, the liver cell nodule began to be observed in liver, and after 10 weeks no normal livers were observed, the nodule ratio of the liver cells was 62.5% and the tumor ratio (that is, the number of samples exhibiting either adenoma or carcinoma, as a percentage of the total number of samples) was 37.5% (adenoma 25%, carcinoma 12.5%). After 24 weeks, the tumor ratio increased to 46.2%.

In the case of Group IV, wherein Himedaka were raised in the DENA solution for 4 weeks and after 2 weeks, a feed containing 500 ppm of GITC was provided thereto, the formation of cancer was retarded. Even after 10 weeks, the normal cell was observed at a proportion of 70%, and the nodule ratio and the tumor ratio of the liver cells were, respectively, 20.8% and 9.2%. After 24 weeks, the normal liver constituted 28.6% of the total, and the nodule ratio and the tumor ratio of the liver cells were, respectively, 50.4% and 19.0%.

By comparing the results of Group IV with those of Group II, wherein GITC of this invention was not used, it can be seen that GITC markedly reduces the formation of hepatic cancer in lower animals and has an excellent effect of treating cancer.

Further, in comparing the results of Groups III and IV with those of Groups V and VI, it can be seen that the GITC compound of the present invention has an excellent hepatic cancer treating effect in lower animals as compared with 5-FU as a conventional cancer treating medicine.

In Group III of Example 1, in order to examine the toxicity of GITC of this invention, each group being comprised of fifty Himedaka were raised by administering a feed (CE-2) containing 500 ppm of GITC in the amount of about 800 mg/day per one group of the fifty Himedaka for a long period of time of 10 to 24 weeks. The results are shown in Group III (GITC Zone) of Table 2 above. From the results, no adverse effects were observed on the Himedaka. It has thus been found that GITC of this invention has almost no toxicity or markedly low toxicity. Further, it can be seen that GITC compound of the present invention has no toxicity even at 5 times dose of 5-Fu as the conventional carcinostatic substance.

As is apparent from the above explanation, it has been found that GITC of this invention greatly inhibits the formation of cancer and an excellent effect of treating hapatic cancer in lower animals.

The GITC of this invention is not only effective for the treatment of hepatic cancer of Himedaka, but also has a similar effect for treatment of hepatic cancer of mammals generally such as mice, rats, etc. This effect can be obtained by 2,3,4,5,6-penta-o-acetyl-D-gluconyl isothiocyanate; similar compounds, such as 2,3,5-tri-o-benzoyl-β-D-ribofuranoyl isothiocyanate and 2,3,4,6-tetra-o-acetyl-β-D-glucopyranozoyl isothiocyanate, seem to have less effect of treating hepatic cancer.

The medicine of this invention has unique hepatic cancer treating effects in lower animals which are not obtained by using other similar compounds, is sufficiently effective to be administered in relatively small amounts, as compared to most conventional cancer treating medicines, and has almost no toxicity. Thus the medicine of this invention is very suitable for the treatment of hepatic cancer in lower animals.

The following Examples 2 and 3 are provided to illustrate the hepatic cancer preventing and treating effects in lower animals of the GITC compound of this invention as described above in greater detail.

EXAMPLE 2

Mice (ICR ♀, 6-weeks-old) were divided into each group being comprised of three mice. A low toxic amount (required to cause carcinogenesis as shown in Table 3) of a carcinogenic substance, 2-fluorenyl acetamide (hereinafter referred to a "2-FAA") was added to a feed (CF-2 produced by Japan CLEA) in combination with GITC or the similar compounds 2,3,5-tri-o-benzoyl-β-D-ribofuranoyl isothiocyanate (hereinafter referred to as "4423") and 2,3,4,6-tetra-o-acetyl-β-D-glucopyranozoyl isothiocyanate (hereinafter referred to as "3886"), and the thus-prepared feed was orally administered to each mouse in the average amount of about 5 g/one mouse/day.

The amount (wt%) of each of 2-FAA, 4423, 3886 and GITC contained in the prepared feed is shown in Table 3. However, the amount of the prepared feed supplied to the mice may vary depending upon the weight of mouse. Therefore, the dose of each substance may vary depending upon the weight of mouse.

The liver disease found in the mice was observed as shown in Table 3.

TABLE 3

| Group | Administration | Observation of Liver |
|---|---|---|
| M-I | 2-FAA (0.05 wt %) + 4423 (0.02 wt %) was administered for 1 week and then 2-FAA (0.1 wt %) + 4423 (0.05 wt %) was administered for 1 week. | Slight vacuolation of liver cell |
| M-II | 2-FAA (0.05 wt %) + GITC (0.02 wt %) was administered for 1 week and then 2-FAA (0.1 wt %) + GITC (0.05 wt %) was administered for 1 week. | Almost normal (only a few liver cell with vacuolation) |
| M-III | GITC (0.05 wt %) alone was administered for 2 weeks. | Normal |
| M-IV | 2-FAA (0.05 wt %) + 3886 (0.02 wt %) was administered for 1 week and then 2-FAA (0.1 wt %) + 3886 (0.05 wt %) was administered for 1 week. | Moderate or slight vacuolation of liver cell |
| M-V | 2-FAA (0.05 wt %) was administered for 1 week and then 2-FAA (0.1 wt %) was administered for 1 week. | Moderate vacuolation of liver cell |
| M-VI | No administration | Normal |

As can be seen from Table 3, the administration of 2-FAA alone (Group M-V) caused moderate vacuolation (clear cell wateration) of liver cell, which suggest a kind of pre-neoplastic change.

In Groups M-I (4423) and M-IV (3886) wherein the similar compounds were added, there was observed the moderate or light vacuolation of liver cell, which indicates that both the compounds have no effect of inhibiting cancer. On the other hand, in Group M-II wherein the medicine of this invention was used, almost all of the mice were normal, and it is thus confirmed that the superior cancer treating effect of the compound of this invention.

In the experiment of Group M-III of Example 2, wherein the toxicity was tested, GITC medicine according to this invention was continuously administered for 2 weeks in an amount of about 100 mg per killogram of the weight of the mouse via the feed (CE-2) containing 0.05% GITC. However, the amount of the feed containing GITC vary depending upon the weight of the experimental animal, i.e., mouse. No mice died and no change in liver cells was observed as a result. From the results as shown in Group M-III of Table 3, no adverse effects were observed on the mice. It has thus been found that GITC of this invention has almost no toxicity or markedly low toxicity.

EXAMPLE 3

Rats (SD type ♂, 5-weeks-old) were divided into each group being comprised of twelve rats. 3'-Methyl-4-dimethylaminoazobenzene (hereinafter referred to as "3'MeDAB") as a carcinogenic substance was added to a feed (CE-2) alone or in combination with GITC, and the thus-prepared feed was orally administered to rats for 23 weeks under the condition as shown in Table 4. The CE-2 produced by Japan CLEA was used as a feed supplied to the rats. 3'MeDAB and GITC were mixed in the amount of 0.06 wt% and 0.05 wt% in the feed, respectively. The average amount of the feed administered to the each rat is about 15 g/one rat/day. However, the administration amount of the prepared feed may vary depending upon the weight of the rat. The results are shown in Table 5 below. From the results of Table 5, it is thus confirmed that the GITC compound of this invention has the superior hepatic cancer preventing and treating effects in lower animals.

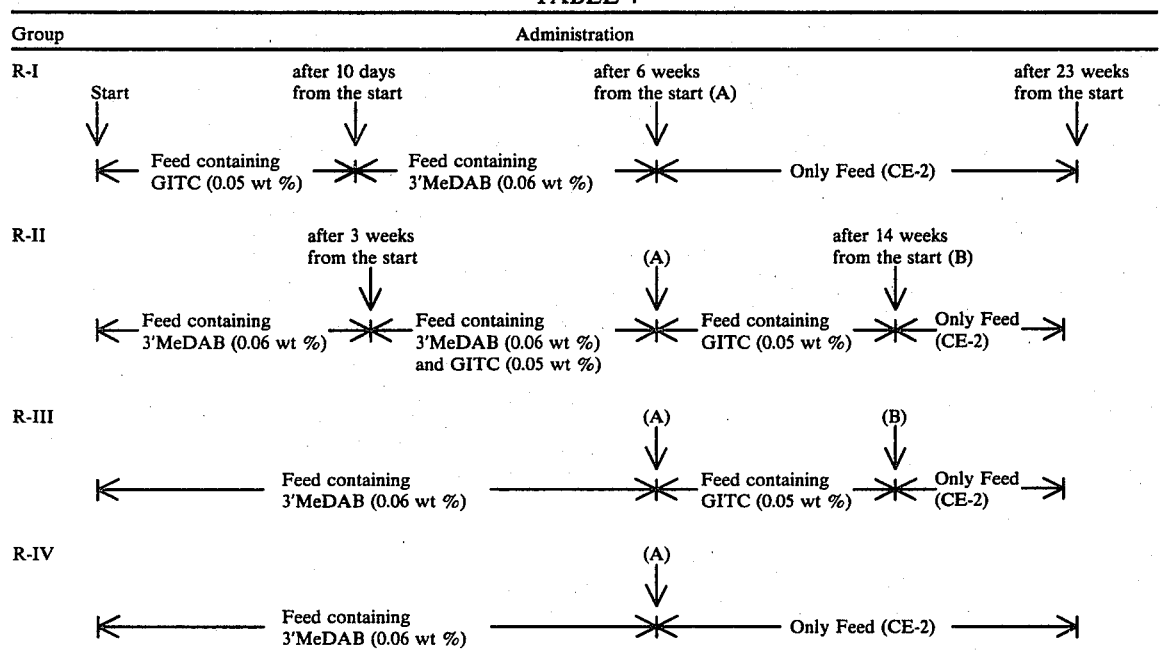

TABLE 4

TABLE 4-continued

| Group | Administration |
|---|---|
| R-0 | ←——————— Only Feed (CE-2) ———————→ |

Note:
The parenthesized wt % is percentage of each substance contained the prepared feed to be supplied to rat.

TABLE 5

| | | R-0 (number of rat) | R-I (number of rat) | R-II (number of rat) | R-III (number of rat) | R-IV (number of rat) |
|---|---|---|---|---|---|---|
| Centrolobular fat change | | | | | | |
| | [±] | 5 | 6 | 5 | 3 | 0 |
| | [+] | 4 | 1 | 2 | 1 | 5 |
| | [++] | 0 | 0 | 0 | 0 | 1 |
| Pleomorphism of liver cell nuclei | | | | | | |
| | [±] | 0 | 0 | 1 | 2 | 0 |
| | [+] | 0 | 2 | 3 | 3 | 11 |
| Hyperplastic focus (are of liver cell) | | | | | | |
| Clear glycogen-storage cells | | | | | | |
| | [±] | 0 | 0 | 1 | 1 | 0 |
| | [+] | 0 | 6 | 5 | 6 | 7 |
| | [++] | 0 | 1 | 0 | 1 | 5 |
| Fat-storing cells (vacuolated cells) | | | | | | |
| | [±] | 0 | 1 | 2 | 1 | 0 |
| | [+] | 0 | 2 | 0 | 4 | 8 |
| | [++] | 0 | 1 | 0 | 0 | 1 |
| Acidophilic cells | | | | | | |
| | [±] | 0 | 1 | 0 | 2 | 1 |
| | [+] | 0 | 0 | 0 | 1 | 3 |
| Basophilic cells | | | | | | |
| | [±] | 0 | 0 | 0 | 1 | 1 |
| | [+] | 0 | 0 | 0 | 1 | 7 |

[±]: slight change
[+]: moderate change
[++]: marked change

While the invention has been described in detail and with reference to specific embodiments thereof, it will be apparent to one skilled in the art that various changes and modifications can be made therein without departing from the spirit and scope thereof.

What is claimed is:

1. A cancer preventing and treating medicinal composition in the form of a capsule, a tablet, a powder, a granule, a vial or an ampule containing
   (1) a therapeutically effective amount of 2,3,4,5,6-penta-o-acetyl-D-gluconyl isothiocyanate for treating hepatic cancer, in lower animals, and
   (2) a pharmaceutically acceptable carrier or diluent.

2. A method of treating hepatic cancer in lower animals comprising administering to said lower animals a therapeutically effective amount for treating said cancer of 2,3,4,5,6-penta-o-acetyl-D-gluconyl isothiocyanate.

3. The method of claim 2, wherein said administering is orally administering.